United States Patent [19]

Metzger

[11] 4,049,898

[45] Sept. 20, 1977

[54] AMPHOTERICIN COMPLEXES CONTAINING OXALIC ACID AND CALCIUM

[75] Inventor: Julio Metzger, East Brunswick, N.J.

[73] Assignee: E. R. Squibb & Sons, Inc., Princeton, N.J.

[21] Appl. No.: 555,015

[22] Filed: Mar. 3, 1975

Related U.S. Application Data

[60] Continuation-in-part of Ser. No. 338,122, March 5, 1973, abandoned, which is a division of Ser. No. 203,037, Nov. 29, 1971, abandoned.

[51] Int. Cl.$^2$ .............................................. C07H 17/08
[52] U.S. Cl. ......................................... 536/17; 424/180; 536/4
[58] Field of Search ............... 260/210 AB; 536/4, 17

[56] References Cited

U.S. PATENT DOCUMENTS

| | | | |
|---|---|---|---|
| 2,631,143 | 3/1953 | Braker et al. | 260/210 AB |
| 3,244,590 | 4/1966 | Schaffner et al. | 260/210 AB |
| 3,928,570 | 12/1975 | Metzger | 536/17 |
| 3,957,754 | 5/1976 | Aszalos et al. | 536/17 |
| 3,965,090 | 6/1976 | Metzger | 536/17 |

OTHER PUBLICATIONS

Chem. Abst. vol. 53, 1959, p. 17,437(g).
Chem. Abst. vol. 55, 1961, p. 2025(c).

*Primary Examiner*—Johnnie R. Brown
*Attorney, Agent, or Firm*—Lawrence S. Levinson; Merle J. Smith; Burton Rodney

[57] ABSTRACT

This invention relates to new forms of amphotericin B which comprise amphotericin B, an acid anion, and calcium ion. These new forms of amphotericin retain the activity of amphotericin and have the particular advantage of being soluble in acidic or alkaline solutions.

4 Claims, No Drawings

AMPHOTERICIN COMPLEXES CONTAINING OXALIC ACID AND CALCIUM

This application is a continuation-in-part of copending application Ser. No. 338,122 filed Mar. 5, 1973, now abandoned, which is a division of application Ser. No. 203,037 filed Nov. 29, 1971, and now abandoned.

BACKGROUND OF THE INVENTION

Amphotericin B is a polyene macrolide compound having antifungal properties. It is produced by cultivation of an organism and extracted from the culture. Amphotericin B is essentially a high molecular weight highly unsaturated, macrocyclic lactone, better known as a polyene macrolide, possessing a chromophore of seven conjugated double bonds. In addition to the large lactone nucleus, amphotericin B has other characteristic groups including an amino sugar. A general discussion of macrolide antibiotics is found in Kirk-Othmer, Encyclopedia of Chemical Technology, Second Edition, Volume 12, pp. 632 et seq., while a general discussion of polyene antibiotics is found in the same work, Volume 16, pp. 133 et seq.

While amphotericin B has been recognized as a valuable material, particularly in its powerful antifungal properties and in the apparent inability of fungus organisms to develop readily any strains or forms that are resistant to amphotericin B, its clinical (therapeutic) use has been limited by lack of adequate water solubility in forms of amphotericin B which are otherwise stable and appropriate.

OBJECTS OF THE INVENTION

It is, accordingly, an object of the present invention to provide a more soluble form of amphotericin B. A further object is to provide a method for preparing these new forms of amphotericin B. These and other objects of the present invention will be apparent from the following description.

DETAILED DESCRIPTION

This invention relates to new soluble forms of amphotericin B which are believed to be complexes, comprising amphotericin B, Ca++ ion, and the anion of an organic, carboxylic acid of up to 20 carbon atoms such as oxalic, succinic or citric acid. This type of solubilized amphotericin B may be obtained by adding the Ca and the organic carboxylic acid to a substantially anhydrous (not over about 1% water) alcoholic solution of amphotericin B. Methanol is a preferred solvent although any water soluble or fully or partially water miscible alcohol may be used. The mixture of amphotericin B, Ca++ ion, and the organic carboxylic acid (containing excess acid), is agitated for a short time, typically from about 2 to about 30 minutes, and the pH then adjusted to neutral with a suitable base, for example, ammonia. The mixture is then heated moderately to from about 35° to about 65° C while mixing for a period of from about 0.5 to about 2 hours. The pH is then readjusted to neutral, if necessary, and the mixture cooled slowly over a period of from about 0.5 to about 4 hours. The resulting solid is filtered and dried. The acid providing the required anion constituent of the complex may be employed as such or in the form of a soluble alkali or alkaline earth metal salt. The Ca ion in the form of a salt (such as calcium chloride) is added in a ratio of from about 0.2 to about 0.8 mol Ca++ per mol of amphotericin B, preferably from about 0.4 to about 0.6 mol per mol of amphotericin B, and most preferably at about 0.5 mol per mol of amphotericin B. The organic carboxylic acid is added in an excess amount, typically from about 0.5 to about 20 mols per mol of amphotericin B, and preferably from about 2 to about 11 mols per mol of amphotericin B; in preferred embodiments of the invention, oxalic acid is added in an amount of from about 5 to about 10 mols and optimally about 8 mols per mol of amphotericin B, succinic acid is added in an amount of from about 5 to about 11 mols and optimally about 8.5 mols per mol of amphotericin B, or citric acid is added in an amount of from about 2 to about 8 mols, and optimally about 5 mols per mol of amphotericin B.

The complex of amphotericin B in accordance with the invention retains the antifungal activity of amphotericin B and is soluble in water. A particular advantage of the complex is that it permits the preparation of more concentrated aqueous solutions for use as such and in processing. Such concentrated aqueous solutions may be used to control fungal growths in the digestive tract of fowl by supplying it in the drinking water, e.g., at a concentration of from about 2 g to about 7 g per liter.

The amphotericin B complex of the present invention is soluble in water under both strongly acidic and strongly alkaline conditions while exhibiting diminished solubility at neutral or near neutral pH. Maximum solubility of the amphotericin B complexes of the present invention occurs at about pH 2 and at about pH 10.

The complexes of the present invention are less soluble in methanol than amphotericin B. Forty mg of the complexes of the present invention are soluble in 750 ml of methanol, whereas 100 mg of amphotericin B are soluble in 750 ml of methanol.

The amphotericin B starting material employed herein may be a crude mycelial powder or a semi-purified intermediate or a pure product.

The following examples illustrate the present invention without, however, limiting the same thereto. All temperatures in this application are expressed in degrees Centigrade unless otherwise indicated.

EXAMPLE 1

Amphotericin B-Calcium-Oxalic Acid Complex 717 g of crude amphotericin B mycelial powder, containing 35.0 g of activity and 0.85% Ca are solubilized in 14 l of methanol by means of 39.9 ml 6 N HCl. The solution is filtered. To this solution (containing 32.6 g of activity) are added 163 ml methanol containing 35.0 g of oxalic acid. The pH is 2.1. After 5 minutes agitation, 51 ml of concentrated NH$_4$OH are added to adjust the pH to 7.0. The mixture is then heated to 45°–50° C and slurried for 1 hour. The pH (6.6) is adjusted to 7.0 by further addition of concentrated NH$_4$OH. The mixture is then cooled to room temperature over a 2-hour period, filtered and the wet cake (95 g) dried overnight under vacuum at 45°–50° C to yield 33.1 g of crystalline complex. This complex has a solubility in water of 3.44g/l at pH 2. This complex exhibits an infrared absorption band at 6.1–6.3 microns which is substantially more intense than a corresponding band of amphotericin B, an $E_1^1$ U.V. absorption value (as methanol solution) of 1500 at 405 millimicrons (as opposed to 1800 for pure amphotericin B), and has an X-ray diffraction pattern.

One hundred mg of the foregoing complex when added to 750 ml of methanol solubilize to the extent of 40%. By way of contrast, 100 mg of amphotericin B are completely soluble in 750 ml of methanol.

One hundred mg of this complex when added to 80 ml of methanol and the pH adjusted to 9.5 (with triethylamine) are soluble to the extent of 35%, whereas 100 mg of amphotericin B are completely soluble in 80 ml of methanol by adjusting the pH to 9.5 with triethylamine.

EXAMPLE 2

Amphotericin B-Calcium-Succinic Acid Complex 10.66 g amphotericin B (938γ/mg of activity-equivalent to 10 g of chemical activity) suspended in 2.5 liters of anhydrous methanol containing 11.1 ml of 5% $CaCl_2$ in methanol (equivalent to 200 mg Ca ion) is solubilized by means of 1.8 ml of 5.8 N HCl (pH 3.9). To the resulting solution are added 100 ml of methanol containing 10 g of reagent grade succinic acid to form a mixture of pH 3.2. The pH of the mixture is adjusted to about 7 by the addition of 7.7 ml concentrated $NH_4OH$. The mixture is then heated to 45°–50° C and slurried for 1 hour and thereafter is cooled to room temperature, filtered and the wet cake dried overnight under vacuum at 45° C to yield 9.1 g of crystalline complex.

The resulting complex contains 2.19% Ca and has a solubility in water of 6.6 g/l at pH 2 as opposed to amphotericin B which has a solubility in water of less than 1 g/l at pH 2. This complex exhibits an infrared absorption band at 6.4μ which can be attributed to the ionized carboxyl group of the complex and is relatively more intense than a corresponding band of amphotericin B, an $E_1^1$ U.V. absorption value (as methanol solutions) of 1622 at 405 millimicrons (as opposed to 1800 for pure amphotericin B), and has an X-ray diffraction pattern.

EXAMPLE 3

Amphotericin B-Calcium-Citric Acid Complex 10.66 g of amphotericin B (938γ/mg of activity-equivalent to 10 g of chemical activity) suspended in 2.5 liters anhydrous methanol containing 11.1 ml of 5% $CaCl_2$ in methanol (equivalent to 200 mg Ca ion) is solubilized by means of 1.75 ml of 5.8 N HCl (pH 3.9). To the resulting solution is added 10.9 g of reagent grade citric acid·$H_2O$ (equivalent to 10 g anhydrous citric acid) to form a mixture of pH 2. The pH of the mixture is adjusted to about 7 by the addition of 7.9 ml concentrated $NH_4OH$. The mixture is then heated to 45°–50° C and slurried for 1 hour and thereafter is cooled to room temperature, filtered and the wet cake dried overnight under vacuum at 45°–50° C to yield 10 g of complex.

The resulting complex contains 1.39% calcium and has a solubility in water of 2.24 g/l as opposed to amphotericin B which has a solubility in water of less than 1 g/l at pH 2. This complex exhibits infrared absorption bands at 6.35μ and 7.2μ which are intensified over corresponding bands of amphotericin B which can be attributed to ionized carboxyl groups of the complex, and $E_1^1$ U.V. absorption value (as methanol solutions) of 1597 at 405 millimicrons (as opposed to 1800 for pure amphotericin B), and has an X-ray diffraction pattern.

In each of Examples 1, 2 and 3, the use of thin layer chromatography makes possible the separation of oxalic acid, succinic acid, and citric acid from their respective complexes with amphotericin B and their detection and positive identification.

What is claimed is:

1. A crystalline amphotericin B complex comprising about 1 mol of amphotericin B, from about 0.5 to about 20 mols of an anion of oxalic acid, and from about 0.2 to about 0.8 mol calcium ion, the complex having a solubility in water at pH 2 of 3.44 g/l, an infrared absorption band at 6.1–6.3 microns, and an $E_1^1$ U. V. absorption value of 1500 at 405 millimicrons.

2. The amphotericin B complex as defined in claim 1 wherein the oxalic acid is employed in an amount ranging from about 2 to about 11 mols per mol amphotericin B.

3. The amphotericin B complex as defined in claim 1 where said calcium ion is present in an amount ranging from about 0.4 to about 0.6 mol per mol of amphotericin B.

4. A method for preparing a crystalline amphotericin B complex as defined in claim 1, which comprises adding from about 0.5 to about 20 mols of an anion comprising oxalic acid, per mol of amphotericin B and from about 0.2 to about 0.8 mol calcium ion per mol amphotericin B to a substantially anhydrous alcoholic solution of amphotericin B, adjusting the pH to neutral, heating to a temperature of from about 35° to about 65° C for a period of from about 0.5 to about 2 hours, adjusting the pH to neutral and cooling slowly over a period of from about 0.5 to about 4 hours.

* * * * *